(12) United States Patent
Hansson et al.

(10) Patent No.: US 8,748,367 B2
(45) Date of Patent: Jun. 10, 2014

(54) USE OF ANTISECRETORY FACTOR

(75) Inventors: Hans-Arne Hansson, Hovås (SE); Eva Jennische, Göteborg (SE); Stefan Lange, Göteborg (SE); Ivar Lönnroth, Mölndal (SE); Peter Eriksson, Göteborg (SE); Anders Persson, Mölndal (SE)

(73) Assignee: AS Faktor AB, Stockholm (SE)

( * ) Notice: Subject to any disclaimer, the term of this patent is extended or adjusted under 35 U.S.C. 154(b) by 873 days.

(21) Appl. No.: 12/659,142

(22) Filed: Feb. 26, 2010

(65) Prior Publication Data
US 2010/0286052 A1    Nov. 11, 2010

Related U.S. Application Data (63) Continuation of application No. 10/573,601, filed as application No. PCT/SE2004/001369 on Sep. 24, 2004, now abandoned.

(30) Foreign Application Priority Data

Sep. 26, 2003  (GB) .................................. 0322645.3

(51) Int. Cl.
*A61K 38/00*  (2006.01)
*A61P 25/00*  (2006.01)
*A61K 38/02*  (2006.01)
*A61K 35/30*  (2006.01)
*C07K 5/00*  (2006.01)
*C07K 14/00*  (2006.01)

(52) U.S. Cl.
USPC ......... 514/1.1; 514/17.7; 514/21.2; 514/21.3; 424/570; 530/300; 530/350

(58) Field of Classification Search
None
See application file for complete search history.

(56) References Cited

U.S. PATENT DOCUMENTS 6,344,440 B1 *  2/2002  Lonnroth et al. ............... 514/5.5
2002/0099016 A1 *  7/2002  Lonnroth et al. ............... 514/12

FOREIGN PATENT DOCUMENTS

WO     WO 97/27296    *    7/1997

OTHER PUBLICATIONS

Johansson et al. JBC 270: 20615-20620, 1995.*
Kempermann et al. Nature 386: 493-495, 1997.*
Wells, 1990, Biochemistry 29:8509-8517.*
Ngo et al., 1994, The Protein Folding Problem and Tertiary Structure Prediction, pp. 492-495.*
Bork, 2000, Genome Research 10:398-400.*
Skolnick et al., 2000, Trends in Biotech. 18(1):34-39.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Barten et al. (Mol Neurobiol. 37: 171-186, 2008).*
Roth et al. (Biol Res 38: 381-387, 2005).*

* cited by examiner

*Primary Examiner* — Daniel E Kolker
*Assistant Examiner* — Aditi Dutt
(74) *Attorney, Agent, or Firm* — Cermak Nakajima LLP; Malcolm K. McGowan (57) ABSTRACT

The present invention relates to the use of an antisecretory protein or homologues thereof having the same properties, or certain fragments thereof in the manufacture of a medicament or a medical food for inducing improved rescue of injured or diseased nervous tissue, proliferation, apoptosis, differentiation and/or migration of an embryonic stem cell, adult stem cell, progenitor cell and/or a cell derived from a stem cell or progenitor cell, for treating a condition characterized by or associated with loss and/or gain of cells. In a preferred embodiment, the condition is a neurotrauma or a condition or disease of the CNS and/or PNS and/or ANS, for example, Alzheimer's disease.

12 Claims, 3 Drawing Sheets

USE OF ANTISECRETORY FACTOR

CROSS REFERENCE TO RELATED APPLICATIONS

This application is a continuation application of a U.S. application Ser. No. 10/573,601, filed Aug. 11, 2006, now abandoned entitled "Novel Use of Antisecretory Factor," which is the national phase of PCT/SE04/01369 filed Sep. 24, 2004, which claims priority to United Kingdom application 0322645.3, filed Sep. 26, 2003, each of which is incorporated herein by reference in its entirety.

FIELD OF THE INVENTION

The present invention relates to the use of peptides, polypeptides and proteins, comprising certain elements of the group of proteins called Antisecretory Factor (AF) in the manufacture of a medicament for treating and/or preventing a condition that is characterised by or associated with the pathological loss and/or gain of cells or hyperproduction or abnormal degradation rate of proteins, expressed in the cell, such as at pathological degeneration, or loss of control of repair, recovery and/or regeneration of differentiated cells and/or tissues, including stem cells or progenitor cells, or medical conditions characterised by or associated with such conditions including damage to the brain and other parts of the nervous system by trauma, asphyxia, toxins, hypoxia, ischemia, infections or degenerative or metabolic insults, resulting in defect, hampered or otherwise abnormal structure and function. It especially relates to a new use of an antisecretory protein or an oligo- or polypeptide or derivatives thereof, a new use of an antisecretory protein inducing food (ref. 15) and a new use of an egg yolk with a high level of antisecretory protein.

Further the present invention relates to a method of propagating, inducing, reducing and/or maintaining the genesis of an isolated stem cell, and a method of treatment.

BACKGROUND OF THE INVENTION

Traumatic, asphyxial, hypoxic, ischemic, toxic, infectious, degenerative or metabolic insults to the central nervous system (CNS), peripheral nervous system (PNS) or autonomic nervous system (ANS) often result in damage to several different cell types. Examples on a degenerative condition in the CNS are Parkinson and Alzheimer disease, either of which often causes loss of specific populations of cells. The former is in particular associated with the specific loss of dopaminergic neurons in the substantia nigra. Similarly, multiple sclerosis is associated with structural and functional affection of axons as well as loss of myelin and oligodendrocytes. Another illustration of a degenerative disorder caused by a loss of neurons is Alzheimer's disease. Additionally, there are many instances in which CNS, PNS and ANS injuries or diseases are associated with damage to oligodendroglia, astroglia, satellite cells, Schwann cells, microglia, vascular cells and neurons.

In general, replacement of neurons and differentiated glial cells following the degeneration or damage is not a characteristic of the adult mammalian brain. Neuronal loss is therefore usually considered permanent. However, it must be stressed that the recovery at diseases, brain tumours and neurotrauma mostly is due to repair and rebuilding of the surviving cells. Nonetheless, postnatal neurogenesis persists well into adulthood in all mammalian species, including man, in the subventricular zone (SVZ) at the lateral ventricles in the brain as well as in the subgranular zone (SGZ) in the dentate gyrus in the hippocampus (Ref. 2, 3, 4). Additionally, there is to a minor extent formation of neural progenitor cells in the spinal cord and in the ANS. It has to be stressed that vascular cells, microglial cells and macrophages as well as connective tissue cells may be rebuilt and formed at injuries to and diseases in nervous tissues.

There exists an omnipotent cell population in the brain, named the progenitor cells, as in other tissues in the body of adult mammals, including humans. Neuronal progenitor cells are stem cells and reside in the subventricular zone (SVZ) at the lateral ventricles of the brain and in the subgranular zone (SGZ) of the dentate gyrus in the hippocampus, where such cells continuously proliferate, and migrate into the adjacent brain structures, and eventually either degeneiate or survive and differentiate. The new-born neurons preferentially in e.g. the SGZ migrate into the granule cell layer of the hippocampus and eventually express markers of differentiated neurons and have morphological characteristics corresponding to differentiated granular cells, establish axonal processes into the mossy fibre pathway and form synaptic connections with their targets in the hippocampus. (Ref. 5) It ought to be stressed that a considerable proportion of such newly formed cells may degenerate if not adequately stimulated, while others gain glial cell characteristics (Ref. 3, 4, 5).

The neurogenesis in the dentate gyrus is in itself especially intriguing as the hippocampus is intimately associated with spatial learning and memory (Ref. 6). The neurogenesis in the SVZ is via the rostral migratory stream supplying the olfactory lobe with new nerve cells, but at e.g. stroke and neurotrauma may the migrating primitive neuronal progenitor cells deviate to the injured or diseased site, if situated in reasonable vicinity to the migrating precursor cells.

The proliferation of progenitor cells in the SVZ and in the SGZ are influenced by e.g. the administration of growth factors, interleukines, N-methyl-d-aspartate (NMDA) receptor antagonist or by the removal of the adrenal glands, which latter results in reduced levels of or absence of corticosteroid hormones (Ref. 7, 8). Additionally, the exposure to an enriched environment is accompanied by an increased number of surviving, newly formed granule cells as well as by increased total number of surviving neurons in e.g. the dentate gyrus (Ref.9). The formation of new nerve cells turns reduced with age (Ref. 3).

Diminishing the inflammatory reaction in a nervous tissue after an injury or a disease is beneficiary and results in an increased number of surviving neurons, improved and extended formation of synapses and reduced astrocytosis, concomitant with less hampering effects on the blood vessels and associated structures and thereby the circulation. A weak to moderate inflammation is beneficial with regard to the repair and to restorative events as well as to the neurogenesis, while a strong inflammation is detrimental and may result in an accentuated loss of cells and tissue, that otherwise might have recovered.

The antisecretory factor (AF) is a class of proteins occurring naturally in the body. The common knowledge of the Antisecretory Factor is summarised by Lange & Lönnroth (Ref. 1.). Its structure and some effects exerted by AF in the body of animals, including in man, is described in patent No WO97/08202 (Ref. 10). The humor AF protein is a 41 kD protein, when isolated from the pituitary gland, comprising 382 amino acids.

The active site with regard to anti-inflammatory one antisecretory effects in AF:s is seemingly localized to the protein in a region close to the N-terminal parts of the AF, localized to no 1-163, or more preferably 36-52 or 36-44, or modifications thereof.

Recent studies, performed by the present inventors, have disclosed that AF are to some extent homologous with the protein S5a, also named Rpn 10, which constitute a subunit of a constituent prevailing in all cells, the 26 S proteasome, more specifically in the 19 S/PA 700 cap. In the present invention AF proteins are defined as a class of homologous proteins having the same functional properties. The proteasomes have a multitude of functions related to the degradation of surplus proteins as well as short-lived, unwanted, denatured, misfolded and otherwise abnormal proteins. Further, the AF/S5a/Rpn10 is involved in the distribution and transportation of cell constituents, most evidently proteins.

Davidson and Hickey (Ref. 11, 12) report in two articles published in 2004 in international, scientific journals, that they had generated an antibody against AF, which modulated inflammatory reactions, confirming the statements in the previous patent application and patent (Ref 10, 14).

SUMMARY OF THE INVENTION

The present inventors have now surprisingly found that AF's and fragments thereof are capable of improving the repair of nervous tissues, as well as mediating and/or reducing the effects of trauma, inflammations and at progressive degenerations, as determined by reduced loss of nervous tissue, and by inhibiting the formation of, or improving the break-down of, β-amyloid and other tissue constituents otherwise accumulating, thereby rescuing the tissue. Beneficial effects have been documented for e.g. vascular constituents as well. AF and fragments thereof are further capable of rescuing nervous tissue constituents and support proliferation of progenitor cells prevailing in the adult CNS. This suggests a new and exiting mode of action in that AF and its fragments could mediate the rescuing and survival of affected cells, as well as facilitating proliferation and migration of stem and progenitor cells in the SVZ and SGZ.

In particular, the inventors have recognized that AF and certain fragments thereof can modulate the destruction, repair, regeneration of nervous tissue constituents, migration and differentiation of progenitor cells and the formation of synapses between existing cells and new cells, facilitating synapse formation and functional recovery as well as decreasing the rate and extent of degeneration and tissue destruction.

The present invention thus provides a new and improved means to treat injuries to, dysfunctions of, diseases in or disorders of the CNS, PNS and/or ANS, inter alia, and thereby provides possibilities for beneficial influence on the function of the tissue.

The brain and spinal cord in adult mammals, including humans, retain the ability to generate neurons throughout life, although that is to a large extent restricted to certain regions only. New neurons, glial cells and tentatively also vascular cells are generated by the proliferation of stem or progenitor cells. During the research leading to the present invention, it became obvious that certain AF fragments rescue nervous tissue, and induced an increased formation of new cells, including processes and synapses between cells.

It has now surprisingly been found that it is possible to treat neural tissue loss after a CNS insult or during the progress of a neuronal disease or disorder by the administration of an effective amount of AF or certain AF fragments. It is thus possible to rescue nervous tissue, and to affect cell formation, migration and differentiation and synapse formation after either neuronal and glial cell loss in the CNS, PNS or ANS, or to prevent the age-related detoriation of said cells in the CNS, PNS and ANS.

In the subsequent text, amino acids are named according to the in biochemistry commonly used abbreviations based on the use of a single letter to identify each amino acid.

In one aspect the present invention relates to the use of an antisecretory protein; or an oligo- or polypeptide or derivatives thereof comprising an amino acid sequence of Formula I:

X1-V-C-X2-X3-K-X4-R-X5 (Formula I; SEQ ID NOS: 3-6)

wherein
X1 is I, amino acids nos. 1-35 of SEQ ID NO: 1, or is absent
X2 is H, R or K
X3 is S or L
X4 is T or A
X5 is amino acids nos. 43-46 (SEQ ID NO: 3), 43-51 (SEQ ID NO: 4), 43-80 (SEQ NO: 5) or 43-163 (SEQ ID NO: 6) of SEQ ID NO: 1, or is absent;
or a pharmaceutically acceptable salt thereof; in the manufacture of a medicament for the treatment and/or prevention of a condition associated with or characterised by rescue or by a pathological loss and/or gain of cells and/or gain of nervous tissue.

In one embodiment of the invention, Formula I has the sequence chosen from one of:
a) amino acids numbers 35-42 of SEQ ID NO:1,
b) amino acids numbers 35-46 of SEQ ID NO:1,
c) amino acids numbers 36-51 of SEQ ID NO:1,
d) amino acids numbers 36-80 of SEQ ID NO:1,
e) amino acids numbers 1-80 of SEQ ID NO:1, or
f) amino acids numbers 1-163 of SEQ ID NO:1
or a pharmaceutically acceptable salt thereof.

SEQ ID NO: 1 is the amino acid sequence of the antisecretory factor polypeptide or protein as given in Johansson, E. et al. (Ref. 13) or Lange, S et al. (Ref. 10, 14)

In a second aspect the present invention relates to the use of an antisecretory protein inducing food in the manufacture of a food or medical food for the treatment and/or prevention of a condition associated with or characterised by rescue or by a pathological loss and/or gain of nervous tissue.

In a third aspect the present invention relates to the use of an egg yolk with a high level, preferably at least 1000 FIL units/ml, of antisecretory protein, in the manufacture of a food or a medical food for the treatment and/or prevention of a condition associated with or characterised by rescue or by a pathological loss and/or gain of nervous tissue.

In one embodiment of the invention the condition is characterised by displaying a pathological degeneration of, loss of ability and/or loss of control of regeneration of and/or loss of control of regeneration of a differentiated cell and/or tissue, an embryonic stem cell, an adult stem cell, a progenitor cell and/or a cell derived from a stem cell or progenitor cell. In still another embodiment the condition is associated with or characterised by a pathological loss and/or gain of cells in the peripheral nervous system, autonomic nervous system and/or central nervous system, and in yet another embodiment the condition is associated with or characterised by rescue or by a pathological loss and/or gain of neural stem cells or neural progenitor cells.

In one embodiment of the invention the condition is associated with or characterised by a pathological loss and/or gain of oligodendroglia, astroglia, Schwann cells, and/or neuronal cells and/or cell populations, and in another the condition is associated with or characterised by a pathological loss and/or gain of non-cholinergic neuronal cells, cholinergic neuronal cells and/or glial cells, and/or cell populations.

In still another embodiment of the invention the condition is caused by damage to the central nervous system or a defect in the central nervous system, and in yet another one the condition is caused by a traumatic, malignant, inflammatory, auto-immune or degenerative disorder.

In a further embodiment the condition is caused by axonal damage caused by concussion, contusion, axonal damage caused by head trauma, axonal damage caused by small vessel disease in the CNS and/or damage to the spinal cord after disease and/or trauma, in another embodiment said condition is characterised by memory loss, and finally in a last embodiment of the new uses the condition is multiple sclerosis, asphyxia, hypoxic injury, ischemic injury, traumatic injury, Parkinson's disease, Alzheimer's disease, stroke or demyelinating disorder.

In a fourth aspect the present invention relates to the use of an egg yolk with a high level of antisecretory proteins according to any one of new uses as described above.

In a fifth aspect the present invention relates to the use of a food and/or drinking solution inducing the formation of antisecretory proteins according to any one of new uses as described above.

In one embodiment the medicament is formulated for intravenous infusion, intramuscular injection and/or subcutaneous injection, in another embodiment the medicament is formulated so that the active substance will pass into the ventricles and/or other cavities at or in a patient's brain when it is administered to said patient, and in yet another embodiment the medicament is formulated so that the active substance will pass into the cerebrospinal fluid of a patient when it is administered to said patient.

In a sixth aspect the present invention relates to a method of propagating, inducing, reducing and/or maintaining the genesis of an isolated stem cell and/or stem cell progeny from any germinal layer in vitro, characterised by treating the isolated cell with an antisecretory protein or an oligo- or polypeptide or derivatives thereof comprising an amino acid sequence of Formula I:

X1-V-C-X2-X3-K-X4-R-X5 (Formula I; SEQ ID NOS: 3-6)

wherein
X1 is I, amino acids nos. 1-35 of SEQ ID NO: 1, or is absent
X2 is H, R or K
X3 is S or L
X4 is T or A
X5 is amino acids nos. 43-46 (SEQ ID NO: 3), 43-51 (SEQ ID NO: 4), 43-80 (SEQ NO: 5) or 43-163 (SEQ ID NO: 6) of SEQ ID NO: 1, or is absent;
or a pharmaceutically acceptable salt thereof.

In one embodiment of the method described above, Formula I has the sequence chosen from one of:
a) amino acids numbers 35-42 of SEQ ID NO:1,
b) amino acids numbers 35-46 of SEQ ID NO:1,
c) amino acids numbers 36-51 of SEQ ID NO:1,
d) amino acids numbers 36-80 of SEQ ID NO:1,
e) amino acids numbers 1-80 of SEQ ID NO:1, or
f) amino acids numbers 1-163 of SEQ ID NO:1
or a pharmaceutically acceptable salt thereof.

In another embodiment of the method said isolated cell is chosen from the group comprising epithelial cells, fibroblasts, osteogenic cells, macrophages and microglial cells, vascular cells, bone cells, chondrocytes, myocardial cells, blood cells, neurons, oligodendrocytes, astroglial cells, progenitor cells, stem cells and/or cells derived from progenitor cells or stem cells.

In a seventh aspect the present invention relates to a method of treatment and/or prevention of a condition associated with or characterised by a pathological loss and/or gain and/or rescue of nervous tissue, comprising administering to a patient in need thereof an effective amount of an antisecretory protein, or an oligo- or polypeptide or derivatives thereof comprising an amino acid sequence of Formula I:

X1-V-C-X2-X3-K-X4-R-X5 (Formula I; SEQ ID NOS: 3-6)

wherein
X1 is I, amino acids nos. 1-35 of SEQ ID NO: 1, or is absent
X2 is H, R or K
X3 is S or L
X4 is T or A
X5 is amino acids nos. 43-46 (SEQ ID NO: 3), 43-51 (SEQ ID NO: 4), 43-80 (SEQ NO: 5) or 43-163 (SEQ ID NO: 6) of SEQ ID NO: 1, or is absent;
or a pharmaceutically acceptable salt thereof.

In one embodiment of the method for treatment and/or prevention, Formula I has the sequence chosen from one of:
a) amino acids numbers 35-42 of SEQ ID NO:1,
b) amino acids numbers 35-46 of SEQ ID NO:1,
c) amino acids numbers 36-51 of SEQ ID NO:1,
d) amino acids numbers 36-80 of SEQ ID NO:1,
e) amino acids numbers 1-80 of SEQ ID NO:1, or
f) amino acids numbers 1-163 of SEQ ID NO:1
or a pharmaceutically acceptable salt thereof.

In another embodiment of the method the condition is characterised by displaying a pathological degeneration of, loss of ability and/or loss of control of regeneration of and/or loss of control of regeneration of a differentiated cell and/or tissue, an embryonic stem cell, an adult stem cell, a progenitor cell and/or a cell derived from a stem cell or progenitor cell, and in still another one the condition is associated with or characterised by a pathological loss and/or gain of cells in the peripheral, autonomic or central nervous system.

In yet another embodiment of the method the condition is associated with or characterised by a pathological loss and/or gain of neural stem cells or neural progenitor cells, and in still another one the condition is associated with or characterised by a pathological loss and/or gain of oligodendroglial, astroglial, Schwann cells, and/or neuronal cells and/or cell populations.

In a further embodiment the condition is associated with or characterised by a pathological loss and/or gain of non-cholinergic neuronal cells, cholinergic neuronal cells and/or glial cells, and/or cell populations, and in still another one the condition is caused by damage to the central nervous system or a defect in the central nervous system.

In one embodiment the condition is caused by a traumatic, auto-immune or degenerative disorder, in another one the condition is caused by axonal damage caused by concussion, contusion, axonal damage caused by head trauma, axonal damage caused by small vessel disease in the CNS and/or damage to the spinal cord after disease and/or trauma, and in still another one said condition is characterised by memory loss.

In one embodiment of the method of treatment and/or prevention the condition is multiple sclerosis, asphyxia, hypoxic injury, ischemic injury, traumatic injury, Parkinson's disease, Alzheimer's disease, stroke or demyelinating disorder.

In another embodiment of the method described above the antisecretory protein or the oligo- or polypeptide or derivatives thereof is formulated into a medicament for intravenous infusion, intramuscular injection and/or subcutaneous injection, in yet another one the antisecretory protein or the oligo- or polypeptide or derivatives thereof is formulated into a medicament so that the active substance will pass into the ventricles and/or other cavities in and/or at a patient's brain when it is administered to said patient, and in a final one the antisecretory protein or the oligo- or polypeptide or derivatives thereof is formulated into a medicament so that the active substance will pass into the cerebrospinal fluid of a patient when it is administered to said patient.

In an eighth aspect the present invention relates to a method of propagating, inducing, reducing and/or maintaining the genesis of an isolated stem cell and/or stem cell progeny from any germinal layer from a patient, characterised by:
a) administering an effective amount of an antisecretory protein or an oligo- or polypeptide or derivatives thereof comprising the amino acid sequence of Formula I as defined above to said patient prior to isolating said cell;
b) propagating said isolated cell in vitro; followed by
c) transplanting said propagated cells into the same or another patient in need thereof.

In a ninth aspect the present invention relates to a method of propagating, inducing, reducing and/or maintaining the genesis of an isolated stem cell and/or stem cell progeny from any germinal layer from a patient, characterised by:
a) isolating said cell and/or stem cell progeny from the patient;
b) administering an effective amount of an antisecretory protein or an oligo- or polypeptide or derivatives thereof comprising the amino acid sequence of Formula I as defined above to said isolated cell in vitro and propagating said cells; followed by
c) transplanting said propagated cells back into the same or another patient in need thereof.

In one embodiment of the two methods just described said isolated cell is selected from the group consisting of fibroblasts, macrophages, vascular cells, bone cells, chondrocytes, myocardial cells, blood cells, neurons, oligodendrocytes, astroglial cells, Schwann cells, progenitor cells, stem cells and/or cells derived from progenitor cells or stem cells.

In some embodiments of the invention, the polypeptides of Formula I may additionally comprise protecting groups. Examples of N-terminal protecting groups include acetyl. Examples of C-terminal protecting groups include amide.

Another embodiment of the invention is to treat conditions associated with insufficient formation of AF:s and related compounds or deficiency of AF receptor function by supplying the individual in an appropriate manner with the required AF, as described above.

It is obvious for any man, skilled in the art, that another embodiment of the invention consists of making use of endogenously produced AF:s. They can be achieved by utilizing the patent describing the method of induction of AF:s by the administration of AF inducing foods (Ref. 15).

Another embodiment of the invention utilizes the administration of egg yolks containing high levels of AF:s, also previously described in a patent (Ref. 16).

DETAILED DESCRIPTION OF THE INVENTION

The term pathological loss and/or gain of cells are in the present context used to describe the common technical feature of a number of medical conditions and disorders. The conditions and disorders are characterised by displaying pathological degeneration of, loss of ability of regeneration of and/or loss of control of regeneration of a differentiated cell and/or tissue, an embryonic cell, an adult stem cell, a progenitor cell and/or a cell derived from a stem cell or a progenitor cell. Additionally, the term further does include improved survival and rescue of nervous tissue cells and reduced or abolished secondary degenerative effects.

The condition to be treated may be caused, inter alia, by one or more of traumatic asphyxia, neuropathic pain, hypoxic, ischemic, toxic, infectious, degenerative or metabolic insults to the nervous system. These often result in damage to several different cell types. Thus damage to brain due to any of the mentioned reasons, frequently causes neurological, cognitive defects and additional psychiatric symptoms. In other cases the conditions may be caused by a traumatic, autoimmune or degenerative disorder or by treatment with drugs or x-ray. In yet other cases, the condition may be caused by genetic factors or the cause may be unknown. In yet further cases, the condition may be caused by axonal damage caused by concussion, axonal damage caused by head or body trauma, axonal damage caused by small vessel disease in the CNS and/or damage to the spinal cord after disease and/or trauma.

In one embodiment of the invention, the condition to be treated is a condition that is associated with or characterised by a pathological Loss and/or gain of cells in the CNS as well as PNS and/or ANS.

Cells that may be affected by a polypeptide comprising a fragment of an amino acid sequence according to SEQ ID NO: 1 are, for example, stem cells, progenitor cells and or even differentiated cells gaining improved survival and regaining transiently lost function. They can belong to any of the three germ layers. Once stimulated the cells will differentiate, gain function and form synapses to replace malfunctioning, dying or lost cells or cell populations, such as in a in pathological CNS, PNS and/or ANS conditions, characterised by abnormal loss of cells, such as glia, and/or neuronal cell or cell populations, such as neuronal cells, and/ or glial cell and/or cell population as well as vascular cells.

The invention particularly relates to the treatment of conditions associated with or characterised by a loss of stem cells, preferably neural stem cells, or conditions characterised by or associated with a loss and/or gain of progenitor cells. Additionally, the invention relates to improved survival of stem or progenitor cells transplanted to nervous tissue.

The invention also relates particularly to the treatment of conditions associated with a loss and/or a gain of differentiated cells. In one preferred embodiment the differentiated cells are bone cells, cartilage cells, cardiomyocytes, oligodendroglia, astroglia, neuronal cells, epithelial cells endothelium, skin, blood, liver, kidney, bone, connective tissue, lung *tissue, exocrine gland tissue, and/or endocrine gland tissue or muscle cells. Preferably, the differentiated cells are neuronal cells, neurons, astrocytes, oligodendrocytes, Schwann cells, or other glial cells.

The invention also provides the use of a polypeptide comprising an amino acid sequence of formula I, in the manufacture of a medicament for rescuing and normalising the cells in the nervous tissue as well as modulating the development of stem cells/progenitor cells, and/or synapses between cells in the CNS, PNS and/or ANS.

A further embodiment of the invention provides a method of modulating the development of stem cells and the synapses between cells in the CNS comprising contacting the stem cells ex vivo or in vivo with an amount of a polypeptide comprising an amino acid sequence of formula 1.

The uses and methods of the invention are preferably suited for the treatment for the treatment of abnormal and/or medical conditions affecting pathological loss or gain of progenitor cells and synapses between neural cells and/or cells derived from neuronal stem cells. The methods may thus be used to prevent, treat or ameliorate damages, diseases or deficits of the CNS, PNS and/or the ANS. The pharmaceutical active substance used according to the invention is especially suitable for the treatment of conditions affecting the Schwann cells, satellite cells, oligodendroglia, astroglia and/or neuronal cells. Such conditions may, e.g. be due to due to CNS damage or deficits, neuronal cell loss or memory loss. Such conditions may, e.g. be caused by a number of different factors or diseases such as traumatic, autoimmune or degenerative disorders, such as multiple sclerosis, hypoxic injury, ischemic injury, traumatic injury, Alzheimer's and Parkinson's disease, and demyelisation disorder. The effect of the pharmaceutically active substance used to this preferred embodiment of the invention is due to their ability to improve cell survival, induce cell formation, synapses generation or the breakdown of neuronal plaque and/or β-APP, β-amyloid and other compounds accumulated in named cells. Nonetheless, and as outlined above, the present invention is not restricted to the uses and methods for treating neuronal diseases and conditions, but said uses and methods may also be used for treating a large variety of mammalian conditions that are characterised by pathological cell loss and/or gain, such as Parkinson's disease, Alzheimer's disease, multiple sclerosis, stroke, asphyxia or hypoxia heart failure.

The pharmaceutical composition or medicament of the invention may additionally comprise one or more pharmacologically acceptable carriers, recipients or diluents, such as those known in the art.

The compositions or medicaments may be in form of, for example, fluid, semi-fluid, semi-solid or solid compositions such as, but not limited to, dissolved transfusion liquids, such as sterile saline, various salt solution, glucose solutions, phosphate buffer saline, blood, plasma or water, powders, microcapsules, micro spheres, nanoparticles, sprays, aerosols, inhalation devices, solutions, dispersions, suspensions, emulsions and mixtures thereof.

The compositions may be formulated according to conventional pharmaceutical practice, taking into consideration the stability and reactivity of oligo- or polypeptides or of the protein.

It is obvious that the compositions can include AF inducing food (ref. 15) or egg yolks, which contain high levels of AF:s. AF inducing foods (ref. 15) are preferably administered orally or perorally in compositions adapted for such a purpose. Egg yolks with levels of AF:s are preferably administered orally or perorally. AF and its derivates may as well be administrated by injections and with the aid of an aerosol or by superficial deposition.

The compositions or medicaments may be formulated according to conventional pharmaceutical practice, see, e.g., "Remington: The science and practice of pharmacy" 20$^{th}$ ed. Mack Publishing, Easton Pa., 2000 ISBN 0-912734-04-3 and "Encyclopedia of Pharmaceutical Technology", edited by Swarbrick, J. & J. C. Boylan, Marcel Dekker, Inc., New York, 1988 ISBN 0-8247-2800-9.

The choice of pharmaceutically acceptable excipients in a composition or medicament for use according to the invention and the optimum concentration thereof may readily be determined by experimentation. Also whether a pharmaceutically acceptable excipient is suitable for use in a pharmaceutical composition is generally dependent on which kind of dosage form is chosen. However, a person skilled in the art of pharmaceutical formulation can find guidance in e.g., "Remington: The science and practice of pharmacy" 20$^{th}$ ed. Mack Publishing, Easton Pa., 2000 ISBN 0-912734-04-3.

The choice of pharmaceutically acceptable excipients in a composition or medicament for use according to the invention and the optimum concentration thereof may readily be determined by experimentation. Also whether a pharmaceutically acceptable excipient is suitable for use in a pharmaceutical composition is generally dependent or which kind of dosage form is chosen. However, a person skilled in the art of pharmaceutical formulation can find guidance in e.g., "Remington: The science and practice of pharmacy" 20$^{th}$ ed. Mack Publishing, Easton Pa., 2000 ISBN 0-912734-04-3.

A pharmaceutically acceptable excipient is a substance, which is substantially harmless to the individual to which the composition will be administered. Such an excipient normally fulfills the requirements given by the national drug agencies. Official pharmacopoeias such as the United States of America Pharmacopoeia and the European Pharmacopoeia set standards for well-known pharmaceutically acceptable excipients.

The following is a review of relevant pharmaceutica compositions for use according to the invention. The review is based on the particular route of administration. However, it is appreciated that in those cases where a pharmaceutically acceptable excipient may be employed in different dosage forms or compositions, the application of a particular pharmaceutically acceptable excipient is not limited to a particular dosage form or of a particular function of the excipient.

Parenteral Compositions:

For systemic application, the compositions according to the invention may contain conventional non-toxic pharmaceutically acceptable carriers and excipients, including microspheres and liposomes.

The compositions for use according to the invention may include all kinds of solid, semi-solid and fluid compositions. Compositions of particular relevance are e.g. solutions, suspensions and emulsions.

The pharmaceutically acceptable excipients may include solvents, buffering agents, preservatives, chelating agents, antioxidants, stabilisers, emulsifying agents, suspending agents and/or diluents. Examples of the different agents are given below.

Examples of Various Agents:

Examples of solvents include but are not limited to water, alcohols, blood, plasma, spinal fluid, ascites fluid and lymph fluid.

Examples of buffering agents include but are not limited to citric acid, acetic acid, tartaric acid, lactic acid, hydrogenphosphoric acid, bicarbonates, phosphates, diethylamine, etc.

Examples of chelating agents include but are not limited to sodium EDTA and citric acid.

Examples of antioxidants include but are not limited to butylated hydroxy anisole (BHA), ascorbic acid and derivatives thereof, tocopherol and derivatives thereof, cysteine, and mixtures thereof.

Examples of diluents and disintegrating agents include but are not limited to lactose, saccharose, emdex, calcium phosphates, calcium carbonate, calcium sulphate, mannitol, starches and microcrystaline cellulose.

Examples of binding agents include but are not limited to sacchaiose, sorbitol, gum acacia, sodium alginate, gelatine, starches, cellulose, sodium carboxymethylcellulose, methylcellulose, hydroxypropylcellulose, polyvinylpyrrolidone and polyetyleneglycol.

The pharmaceutical composition or the substance used according to the invention is preferably administered via intravenous peripheral infusion or via intramuscular or subcutaneous injection into the patient or via buccal, pulmonary, nasal or oral routes. Furthermore, it is also possible to administer the pharmaceutical composition or the pharmaceutically active substance through a surgically inserted shunt into a cerebral ventricle of the patient.

In one embodiment of the present invention, said pharmaceutical composition is formulated so that the active substance will pass into the ventricles of a patient's brain.

In one embodiment of the present invention, said pharmaceutical composition is formulated so that the active substance will pass into the ventricles of a patient's brain or into the cerebrospinal fluid of said patient, when it is administered to said patient. This may e.g. be achieved by mechanical devices, vectors, liposomes, lipospheres, or biological or synthetical carriers.

Preferably, the administered dosage range is about 0.001-100 mg of a polypeptide comprising the amino acid sequence of Formula I per 100 g body weight, comprising a range of 0.001-100 mg/1g, 0.001-100 mg/10 g and 0.001-100 mg/50 g body weight. Preferably, the administered dosage range is about 0.001-100 mg of a polypeptide comprising the amino acid sequence of Formula I per 1 kg body weight.

When food inducing AF:s (ref. 15) are used, the administered dosage correspond to 0.2-5 g of malted cereals per kg of bodyweight. When egg yolks with high levels, i.e. at least 1000 FIL units/ml, of AF:s are administered a dosage of 0.05-0.5 g per kg of bodyweight are used. The response of the individual should be controlled.

The invention may be used to treat humans or non-human mammals.

The terms "treatment" or "treating" as used herein relate to both therapeutic treatment in order to cure or alleviate a disease or a medical condition, characterised by abnormal loss and/or gain of cells, and to prophylactic treatment in order to prevent the development of a disease or a medical condition, characterised by pathological loss and/or gain of cells and cell constituents, e.g. synpapses. Thus both prophylactic and therapeutic treatments are included in the scope of the present invention. The terms "treatment" or "treating" also refer to the effecting of cell genesis from stem cells or progenitor cells by inducing the genesis of differentiated cells, such as e.g. neurons and/or glial, cells after either neuronal, oligodendroglial or glial cell loss in the CNS, PNS or ANS, or to prevent the normal age-related deterioration in the CNS, PNS or ANS or other structures in the body. The treatment may either be performed in an acute or in a chronic way.

AF-expanded stem and/or progenitor cells may be propagated and either pre-differentiated prior to grafting or allowed to differentiate as a result of interactions between the transplanted cells and the host. AF-expanded stem cells and/or progenitor cells may be administered and/or grafted at a single time, or delivered repeatedly over a prolonged period. This will be especially useful if stem cells and/or progenitor cells are administered to enter the target organ via the bloodstream.

According to another preferred embodiment of the invention, it is possible to use a'polypeptide comprising the amino acid sequence of Formula I to propagate progenitor cells or stem cells or other cells in a tissue culture or a cell culture. Such cells may thereafter be used for cell transplantation into a patient suffering from e.g. neuronal cell loss or a condition due to lack of endogenous cells of another type. The cells used to start the culture may either originate from the patient or from another human or animal donor, and may be used in the treatment of a broad variety of diseases and disorders comprising heart diseases such as infarct, diabetes, or in an assortment of neurological diseases and disorders, such as those referred to above.

Thus the invention also provides a method of propagating, inducing, reducing and/or maintaining the genesis of an isolated stem cell and/or stem cell progeny in vitro, characterised by treating the isolated cell with a polypeptide comprising the amino acid sequence of Formula I. Preferably, the isolated cell is selected from the group comprising epithelial cells, fibroblasts, osteogenic cells, macrophages and microglial cells, chondrocytes, myocardial cells, blood cells, neurons, oligodendrocytes, astroglial cells, progenitor cells, stem cells and/or cells derived from said cells. In general, the isolated cell will be treated under appropriate conditions and for a time, which is sufficient to achieve the desired propagation, induction, reduction and/or maintenance.

When cells are to be removed from a patient for in vitro propagation, it may be advantageous first to increase the number of progenitor cells in the patient. This will better facilitate the subsequent isolation of said cells from patients. The number of progenitor cells is increased by use of the method or pharmaceutical composition according to the invention.

A polypeptide comprising the amino acid sequence of Formula I, may be used alone or conjunction with other medicaments, interleukins or e.g. growth factors such as epidermal growth factor (EGF), transforming growth factor (TGF), platelet derived growth factor (PDGF), fibroblast growth factor (FGF) or insulin-like growth factor (IGF), designed to induce cell genesis or proliferation e.g. in the CNS, PNS or ANS. A polypeptide comprising the amino acid sequence of Formula I, alone or in conjunction with other medicaments, peptides, growth-factors, steroids, lipids, glycosylated proteins or peptides, used either simultaneously or in sequence, may be used in order to facilitate cell genesis or the generation of specific cell types in vivo or in vitro. It may also be used to induce immature or multipotent cells to activate specific developmental programs as well as specific genes in the aforementioned cells.

By the above mentioned term "cell genesis" is meant the generation of new cells such as neurons, oligodendrocytes, Schwann cells, satellite cells and astroglial cells from multipotent cells, progenitor cells or stem cells within the adult CNS or PNS or other organs of the body, in situ or in isolation.

Furthermore, the invention also relates to the therapeutic use of substances that decrease the amount of active AF or naturally occurring analogous of AF in the patient and thus decrease the genesis of new cells, e.g. of oligodendrocytes in patients with axonal or spinal cord injury, such as axonal damage caused by concussion, axonal damage caused by head trauma, axonal damage caused by small vessel disease in the CNS, and/or damage to the spinal cord after disease and/or trauma. Examples of such substances are drugs, antibodies, compounds, peptides and/or inhibitor of endogenous AF release.

Since AF supports the genesis of new cells and especially neurons in the hippocampus, a structure intimately coupled to learning and memory, a polypeptide comprising the amino acid sequence of Formula I may be used in order to facilitate learning and memory by the genesis of said cells.

Whilst the present invention relates primarily to a method for treating abnormal conditions in the CNS or PNS that are characterised by pathological loss and/or gain of cells, by affecting neural stem cells or progenitor cells, the uses and methods of the invention may be equally useful for treating and/or preventing medical conditions in other organs of the body, provided that said medical conditions characterised by pathological loss and/or gain of cells.

Whilst reference has primarily been made herein to the use of polypeptides comprising an amino acid sequence of Formula I, the invention relates, mutatis mutandis, also to polypeptides consisting essentially of an amino acid sequence of Formula I, and to polypeptides consisting of an amino acid sequence of Formula I.

The polypeptides comprising an amino acid sequence of Formula I may be produced by standard means, including recombinant and synthetic routes.

The invention will be more fully understood when reading the following Examples, which are intended merely to illustrate, but not to limit, the scope of the invention.

EXAMPLES

Example 1

Induction of Elevated AF Formation Increased the Neurogenesis

The following experiment was performed to assess whether administration of AF influenced the neurogenesis in the brain of a normal adult mammal: the rat.

Rats (body weight 180-350 g at the start of the experiments), male and female, were purchased from B & K AB, Stockholm, Sweden. The animals were kept in cages of approved type and size, and the light was on from 06 to 18. The regional animal experiments ethical committee granted permission for the experiments. Measures were taken to reduce discomfort and pain.

Figure 1:
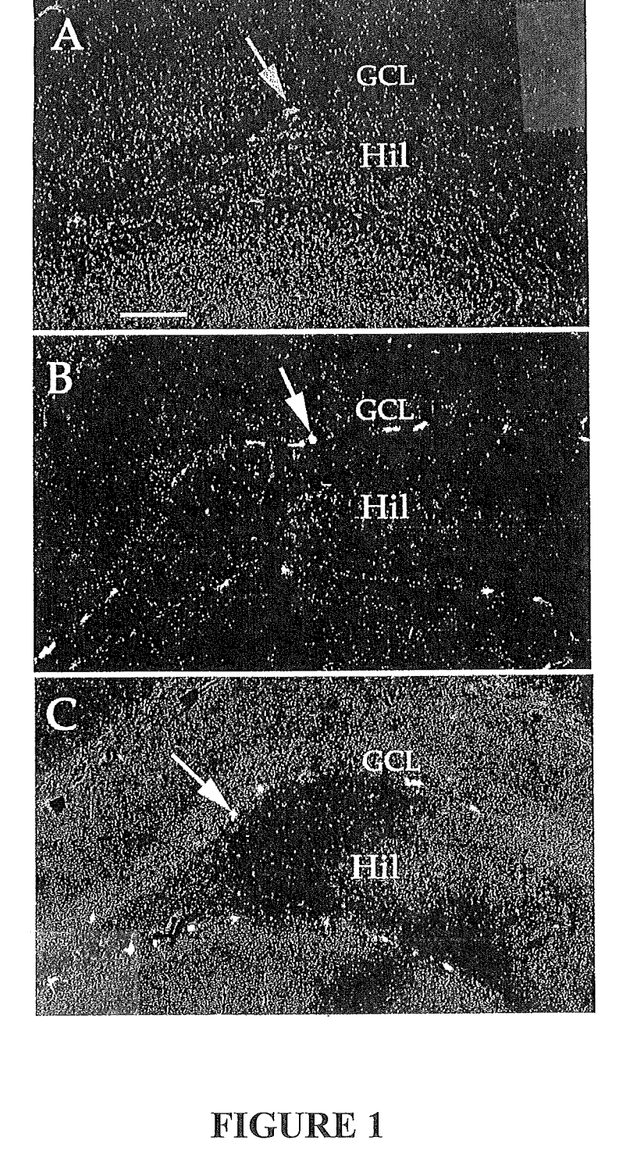
FIG. 1. Confocal immunofluorescence micrographs of dentate gyrus from a sham treated control brain (A) and after seizures induced by intraabdominal injection of kainic acid (10 mg/ml) in buffered saline (B—7 d; C—28 d), disclosing the distribution of proliferating cell clusters. The newly formed cells are stained dark. The number of ribonucleotide reductase (RNR) positive cells, i.e. mitotic, in the SGZ is significantly increased at 7 d (B), and at 28 d (C) after seizures. The insert in B is from one another section of the same brain stained with the same approach method, illustrating two positive=mitotic cell clusters. GCL=granular cell layer, Hil=hilus. Scale bar=200 µm (A, B, C), 20 µm (insert in B).

The test rats were fed on SPC pelleted food and drinking an extract of SPC for at least 10 days prior to sacrifice. The animals were not exposed to any surgery or otherwise manipulated. The rats were anaesthetized by either an intraabdominal injection of an overdose of pentobarbital sodium in saline or by the inhalation of isofluorane. The thoracic cavity was opened, the left ventricle of the heart canulated and a tempered balanced buffered salt solution, with heparin added, infused to rinse the vascular system from blood. Thereafter, a buffered formaldehyde solution in saline was infused to fix the tissue. Eventually, the brain, spinal cord, retina and additional parts of nervous tissues were dissected and further fixed over night in buffered formalin in the cold. The next day, the forebrain and the hippocampus were dissected, rinsed and immersed in buffered saline with 20% sucrose added prior to sectioning in a cryostate microtome. The thin sections, 5-25 µm thick, were then processed for immunohistochemical demonstration of the distribution and prevalence of the R1 subunit of ribonucleotide reductase (RNR) (FIG. 1a), an enzyme of key importance for any DNA synthesis, disclosing cell formation by mitosis (Zhu, H., et al., Ref. 4). In parallel, additional tissue specimens from the forebrain and the hippocampus were embedded in paraffin and processed as described above.

Light microscopy of sections processed for RNR immunohistochemistry disclosed that treatment of normal adult rats for at least 10 days with SPC food increased the occurrence of proliferating stem cells and progenito/cells in the SGZ in the hippocampus, as compared to animals having been supplied with standard rodent pellets. Elevated frequency of dividing cells could be revealed as well in the SVZ in the forebrain. The identity of the newly formed cells was disclosed immunohistochemically with the aid of antibodies against doublecortin (expressed by migrating, immature nerve cells), NeuN (expressed by mature nerve cells), and GFAP (expressed by astrocytes).

It is concluded that supplying adult mammals with SPC food for at least 10 days seemed to markedly promote the proliferation of stem and progenitor cells in the adult brain.

Example 2

Model for Brain Injury by Application of a Freezing Probe

The following experiment was performed to assess the damage caused on the rodent brain by the application of a very cold probe on the outside of the skull bone Rats (body weight 180-350 g at the start of the experiments), male and female, were purchased from B & K AB, Stockholm, Sweden. The animals were kept in cages of approved type and size, and the light was on from 06 to 18. The regional animal experiments ethical committee granted permission for the experiments. Measures were taken to reduce discomfort and pain.

The rats were anaesthetized by the inhalation of isofluorane, and had their heads shaved. The skin was cut open in the mid sagittal plane on the skull. The calvarium was exposed on the left side between the bregma and the lambda. The periostium was detached from the bone, which then was rinsed.

Thereafter, great care was taken to remove blood and any fluid from the calvarium as that may impair the subsequent procedure. A probe made of brass, having a cylindric 4 mm long end piece with a diameter of 3 mm, was cooled by immersion in a standardized manner in liquid nitrogen. The cooled probe was thereafter applied for 40 s on the calvarium in between the lambda and bregma, 4 mm lateral to the sagittal mid line. The probe was then removed and the skin wound sutured. The application of the freezing probe resulted transiently in that the brain tissue underlying the exposure site turn frozen. It ought to be stressed that the skull was not opened and no fractures or other signs of gross damage induced. The animals moved afterwards without any obvious problems, behaved normally and ingested food and drinking fluid close to as those untreated, after having recovered from the anaesthesia.

Figure 2:
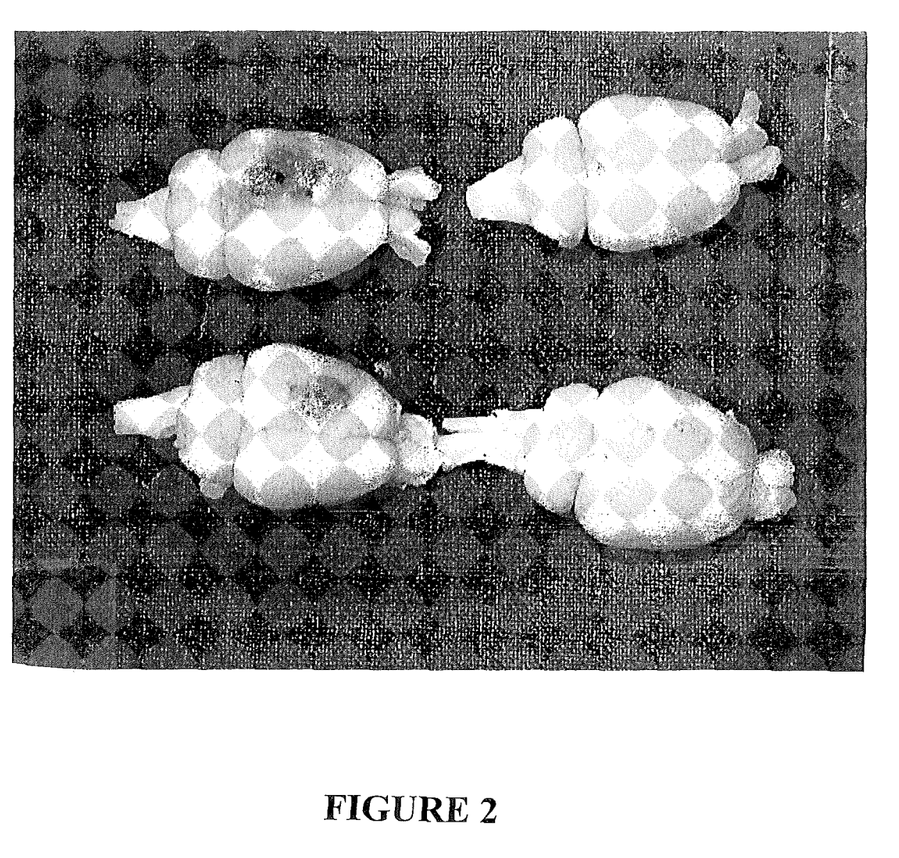
FIG. 2. Photo of brains from rats 2 days after that a freezing probe had been positioned for 40 seconds on the outside of their skull bone. The two brains in the upper row had had free access to standard pellets and tap water prior to and after the brain injury. Note the bleedings and the discoloured brain tissue. The two brains in the lower row had had unlimited access to SPC food and drinking solution for 12 days prior to the exposure of the outside of the skull bone to a freezing probe and then for the next two days, prior to sacrifice. Note the absence of macroscopic bleeding and the less extensive brain damage. The high AF levels in the rats fed on SPC reduced the brain damage, as further confirmed by light microscopy of stained sections.

At 2 days after the freezing injury the left cerebral cortex showed discoloration and bleeding in an area with a diameter of 3-5 mm, immediately underneath the part of the skull bone exposed to the cooling (FIG. 2). A shallow depression indicated that there was a loss of nervous tissue. There is an oedema in the penumbra, i.e. the brain substance bordering the central zone of severely injured nervous tissue. The oedema could at closer inspection be revealed to be spread to the white matter, most evidently on the same side as injured. Light microscopic examination of stained, thin sections disclosed necrotic tissue in the centre of the injured cerebral cortex, with oedema which is likely to add to the secondary tissue and cell damage in the penumbra. The primary damage is the one taking place during the first few seconds after the application of the freezing probe. The secondary brain damage comprises changes taking place after a minute or more, the exact time being defined depending on the type of injury. The secondary changes may turn out to become more severe with time, especially if there is a brain oedema, which tend to be deleterious. There was an inflammatory reaction starting within minutes, most evidently in the penumbra, and characterised by the appearance of an increasing number of activated astrocytes and microglia cells. The blood vessels were also damaged but rapidly rebuilt. However, the necrotic, central part of the injured tissue was not revascularised until after days or even weeks.

Any injury to the brain inducing an inflammation causes a transient elevation of the stem and progenitor cell proliferation in the SGZ and in the SVZ, if those areas are not badly impaired. Further, the new neural stem and progenitor cells must be stimulated in order to survive, migrate, and differentiate; otherwise the cell proliferation may result in a net loss of neuronal cells.

Concomitantly, there is an accumulation of beta amyloid precursor proteins (β-APP) and beta-amyloid (Aβ), formed as a result of the brain injury and accumulating in nerve cells bodies and processes. β-APP and A β are both toxic to nerve cells and start to accumulate within a few hours after a neurotrauma. However, if these two proteins dissolve and thus disappear, the possibility for the affected nerve cells to survive, recover, and reintegrate structurally and functionally must be considered as highly beneficial. Further, cytoskeletal constituents, such as neurofilaments and microtubules, are suffering at a neurotrauma and accumulate, forming aggregates and tangles, which make the primary injury worse and even deleterious. Axons and dendrites appear as being irregularly beaded, swollen and distorted due to the focal accumulation of cytoskeletal constituents, cell organelles and amyloid. Due to the disorganisation of nerve cells after a trauma, such as that due to freezing, the normal very precise and regular organisation of the cell machinery is lost in parts and normal cell constituents may accumulate or appear in abnormal concentrations, such as ubiquitin. Nerve cells do normally not divide, with the exception of those in the SGZ and SVZ, but may after a neurotrauma start to form proteins and other compounds in abnormally high amounts, such as i.e. cyclins and related constituents, normally only prevalent in dividing cells.

The glial cells, the astrocytes and the microglial cells, proliferated and turned hypertrofic. There was further a rebuilding of the residuing blood vessels and angiogenesis in the injured tissue.

The oedema that is appearing after any neurotrauma aggravates the injury to the tissue (secondary damage).

At six days after the freezing injury (FIG. 2) there is a shallow cavity in the centre of the injured cortex due to loss of brain tissue. Minute residues of the bleeding may be recognized, but most of the extravasated blood was removed. The necrosis in the centre of the injury was in parts cleaned from debris and therefore looked as a fairly distinctly delimited depression. The penumbra, enclosing the central necrosis, is rich in microglial cells and hypertrophic, proliferating astrocytes. Injured and dying nerve cells are seen in the penumbra as well as surviving ones. Most nerve cells show accumulation of neurofilaments, β-APP and Aβ. It is concluded that the freezing of the brain through the intact skull bone results in a reproducible manner in damage to the brain.

Example 3

AF:s Rescue Freeze-Injured Brain Tissue, as Investigated After 2 Days

The following experiment was performed to assess if increased occurrence of AF in a body affected the extent and severity of a brain injury caused on the rodent brain by the application of a freezing probe on the outside of the skull bone, exerted neuroprotection.

Rats (body weight 180-350 g at the start of the experiments), male and female, were supplied with SPC food and drinking fluid for at least 10 days prior to the brain injury. At the day of injury, the rat were anaesthetized and prepared as described in experiment 2. The freezing probe was applied once for 40 seconds. After suturing the skin wound in the skull and recovered from the anaesthesia, the rats were allowed to move freely and had access to SPC food and drinking fluid.

Two days after the freezing injury, the rats were sacrificed and fixed by perfusion as described. When opening the skull bone, it became obvious that there was less extensive brain injury as compared to that in the animals having had commercial standard pellets and tap water (FIG. 2). There were minute bleedings only to be recognized. Further the shallow depression of the central parts of the injured area was not obvious. The penumbra appeared to be affected by less oedema, than that observed in animals fed on standard pelleted food and tap water. Light microscopic investigation of thin, stained sections through the injured brain tissue disclosed less extensive occurrence of damaged cells and only minor extravasation of blood elements. Irregularly distributed swellings and beadings were sparse. The otherwise prominent accumulation of e.g. amyloid and neurofilaments was less marked. The gliosis was less prominent that in the reference animals, supplied with standard food and tap water. However, there was a certain variation in the extent of the neuroprotection exerted by the SPC food and drinking fluid after two days.

It is concluded that the experimental induction of increased formation of AF in a body results in neuroprotection as disclosed by reduced brain tissue damage after a focal injury, investigated after 2 days.

Example 4

AF:s Rescue Freeze-Injured Brain Tissue, as Investigated After 6 Days

The following experiment was performed to assess if increased occurrence of AF in a body affected the extent and severity of a brain injury caused on the rodent brain by the application of a freezing probe on the outside of the skull bone, exerting neuroprotection.

Rats (body weight 180-350 g at the start of the experiments), male and female, were supplied with SPC food and drinking fluid for at least 10 days prior to the brain injury. At the day of injury, the rat were anaesthetized and prepared as described in experiment 2. The freezing probe was applied once for 40 seconds. After suturing the skin wound in the skull and recovered from the anaesthesia, the rats were allowed to move freely and had access to SPC food and drinking fluid.

Figure 3:
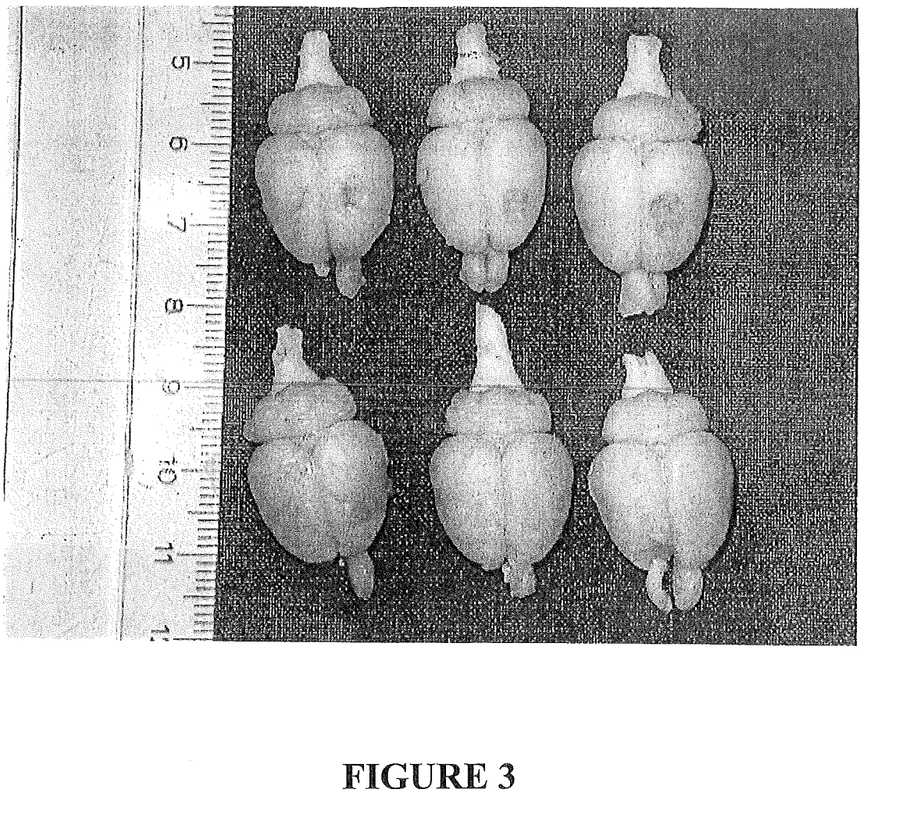
FIG. 3. Photo of brains from rats 6 days after that a freezing probe had been positioned for 40 seconds on the outside of their skull bone. The three brains in the upper row are from adult rats that had had free access to standard pellets and tap water prior to and after the brain injury. Note the minor bleedings and the shallow defect in the brain tissue. The three brains in the lower row had had unlimited access to SPC food and drinking solution for 5 days prior to the exposure of the outside of the skull bone to a freezing probe and then for the next six days, prior to sacrifice. Note the less extensive brain damage, as compared to the rat brains in the upper panel. The AF levels in the rats fed on SPC for 5 days prior to the freezing injury reduced the brain damage, as further confirmed by light microscopy of stained sections.

Six days after the freezing injury, the rats were sacrificed and fixed by perfusion as described. When opening the skull bone, it became obvious that there was less extensive brain injury as compared to that in the animals having had commercial standard pellets and tap water (FIG. 3). There were no bleedings to be recognized. Further the shallow depression of the central parts of the injured area was not marked and in some cases difficult to identify for certain. The penumbra appeared to be affected by less oedema, than that observed in animals fed on standard pelleted food and tap water. Light microscopic investigation of thin, stained sections through the injured brain tissue disclosed less extensive occurrence of damaged cells and rarely any residing extravasation of blood. Irregularly distributed swellings and beadings of axons and dendrites were sparse. There was a distinct astrogliosis in the penumbra region, but not as extensive and widespread as in the corresponding brains from rats having had standard pellets and tap water. There was, however, a variation in the extent of the neuroprotection exerted by the SPC food and drinking fluid.

When investigating the hippocampus, there was a marked increase in the proliferation of neural stem and progenitor cells in the SGZ. The same was true for the SVZ, but less obvious.

It is concluded that the experimental induction of increased formation of AF in a body results neuroprotection as disclosed by reduced brain tissue damage after a focal injury, less prominent gliosis and increased formation of new nerve cells from stem cells and progenitor cells in, most evidently, the SGZ, as investigated after 6 days.

Example 5

Daily Intravenous Injections of a Derivate o. AF (a 16 Amino Acid Peptide) Rescue Freeze-Injured Brain Tissue, as Investigated After 6 Days The following experiment was performed to assess if increased occurrence of AF in a body affected the extent and severity of a brain injury caused on the rodent brain by the application of a freezing probe on the outside of the skull bone, exerted neuroprotection.

Rats (body weight 180-350 g at the start of the experiments), male and female, were supplied with standard pelleted food and tap water prior to and after the brain injury. At the day of injury, the rat were anaesthetized and prepared as described in experiment 2. The freezing probe was applied once for 40 seconds. After suturing the skin wound in the skull and recovered from the anaesthesia, the rats were allowed to move freely.

All rats received twice daily for 5 days, starting on the day of surgery, an intravenous injection of 1-10 μg per kg body weight of a synthetic peptide, being a fragment of AF, comprising amino acids 36-51, i.e. composed of 16 amino acids. It was dissolved in saline and prepared freshly prior to each injection. There was no intravenous injection of the peptide on the day of sacrifice, day 6. No side effects with regard to motor activity, explorative behaviour, food intake or drinking habits could be observed for any of the animals.

Six days after the freezing injury, the rats were sacrificed and fixed by perfusion as described. When opening the skull bone, it became obvious that there was less extensive brain injury as compared to that in the animals having had commercial standard pellets and tap water. There were no bleedings in or on the brain. Further the shallow depression of the central parts of the injured area was not marked and in some cases difficult to identify for certain. The penumbra appeared to be affected by minor oedema. Light microscopic investigation of thin, stained sections through the injured brain tissue disclosed less extensive occurrence of damaged cells and rarely any residing extravasation of blood than observed in the brains from rats treated and investigated as in experiment 2. Irregularly distributed swellings one beadings of axons and dendrites were sparse. There was a distinct astrogliosis in the penumbra region, but not as extensive and widespread as in the corresponding brains from rats having had standard pellets and tap water. There was, however, a variation in the extent of the neuroprotection exerted by the injected peptide.

When investigating the hippocampus, there was an increased proliferation of neural stem and progenitor cells in the SGZ. The same was true for the SVZ.

It is concluded that the intravenous daily injections of a fragment of AF during the first 5 days after a freezing injury results in neuroprotection as disclosed by reduced brain tissue damage after a focal injury, less prominent gliosis and elevated formation of new nerve cells from stem cells and progenitor cells in most evidently the SGZ, as investigated after 6 days.

Example 6

AF Rescue Brain Tissue, Injured by the Excitotoxic Drug Kainic Acid, as Investigated After 6 Days The following experiment was performed to assess if increased occurrence of AF in a body affected the extent and severity of a brain injury, caused on the rodent brain by the intraperitoneal injection of the excitotoxic compound kainic acid, exerted neuroprotection.

Rats (body weight 180-350 g at the start of the experiments), male and female, were supplied with SPC food and drinking fluid for at least 10 days prior to the brain injury. The same number of rats got in parallel standard pelleted food and tap water, for comparison.

At the day of injury, kainic acid (Sigma Chemical Co, St. Louis, Mo., USA), dissolved in buffered saline, and at an amount of 10 mg/kg body weight, was injected once into the abdomen. Thereafter, the rats were allowed to move freely and had access to SPC food and drinking fluid. After 45-60 minutes, the rats started to behave stereotypically, performing repeatedly one or two movements. Thereafter, they got unilateral and generalized seizures. The rats were closely monitored and the extent of affection recorded. At 3 hours after the kainite treatment, diazepam was injected to stop the seizures. Only rats exerting a standardised type and extent of seizures were included in the present study.

Six days after the seizures, the rats were sacrificed and fixed by perfusion as described. When opening the skull bone, no signs of brain damage could be disclosed. There was no difference between those having had SPC food and those fed on standard pellets and tap water. There was no macroscopically demonstrable oedema in either case.

Light microscopic investigation of thin, stained sections through the hippocampus of the brains disclosed differences in the extent of damage between the two groups of animals. Those treated with SPC food showed less extensive degeneration of nerve cells in the CA1 and CA3/4 regions as compared to those more severely injured having had standard pellets and tap water. The same difference could be discerned for the sprouting of mossy fibres. Irregularly distributed swellings and beadings of axons and dendrites were recognized. There was as well a less prominent astrogliosis in the hilus region and in the stratum lacunosum and the stratum moleculare as well as in the hilus in rats having been fed on SPC food, as compared to those having had standard pellets. There was, a considerable variation in the extent of the neuroprotection exerted by the SPC food and drinking fluid.

When investigating the hippocampus, it was obvious that there was an increased proliferation of neural stem and progenitor cells in the SGZ (FIG. 1). The same was true, although less prominent, for the SVZ. There was an increased rate of survival of the newly formed RNR-positive cells in the SGZ after feeding with SPC food and drinking solution.

It is concluded that the experimental induction of increased formation of AF in a body resulted in neuroprotection, as disclosed by reduced extent of the brain tissue damage in the hippocampus at 6 days after seizures, and concomitantly less prominent gliosis and increased formation of new nerve cells from stem cells and progenitor cells in most evidently the SGZ.

Example 7

Effects of AF and AF Fragments on the Rescue of Brain Tissue, After a Diffuse Brain Injury, Most Evidently on the Diffuse Axonal Injury.

The following experiment is to be performed to assess if increased occurrence of AF or AF fragments in a body affected the extent and severity of a diffuse brain injury, caused by a rotational acceleration trauma to a rabbits head.

The most common brain injury is that named brain concussion. It affects 80.000-90.000 Swedes annually and of those about every fourth had to stay in a hospital for at least a day for clinical examination and observation. The corresponding figures for the USA is that about 2 million individuals suffer from brain concussion and of those roughly half a million stay in a hospital for a day or more. A large number of those affected are investigated by x-ray, and/or MRI.

After a brain concussion there is at an increased risk for such individuals to suffer for long time periods of neuropsychiatric sequele and pain. Further, there is an increased risk for subsequent development of dementia, most evidently Alzheimer's disease.

Young and adult rabbits will be used. Anaesthetized rabbits will have their skull bone freed from soft tissue. A helmet, made of plastic and reinforced with glass fibres, will be glued to the skull bone. The helmet is connected to a exposure equipment, that transmit a rotational acceleration trauma to the head, either anterior-posterior or the reverse. The rabbits will be treated by administration of AF or synthetic peptides corresponding to selected sequences of AF. Additional rabbits will be fed SPC food and drinking solution or alternatively compositions based on egg yolk. The exposure parameters will be closely monitored by a computerised recording system.

At predefined time periods after the rotational acceleration trauma, the brains will be removed from sacrificed rabbits and carefully investigated for presumed neuroprotective effects by the AF and its derivates as well as egg yolk. The advantage of the planned experiments is that the brain injury is standardized and correspond to that most frequent for human beings, a brain concussion. The formation of brain oedema will be closely monitored by the intracerebral implantation of fibre optic sensors, connected to a computer. Thereby, the effects of AF and its derivates on the oedema formation and histopathological abnormalities can be closely followed and documented. Long-term studies will as well be performed.

It is concluded that the experimental induction of a diffuse brain injury, which is treated with AF or derivates thereof, is of key importance for the evaluation of neuroprotective long-term effects on the simulated condition, which in clinical medical practice is being the dominant cause of brain injury in humans.

REFERENCES

1. Lange, S. & Lönnroth, I. Int. Review of Cytology 210 39-75 (2001)
2. Eriksson, P. S. et al.: Nature Med. 11: 1313-1317 (1998)
3. Kuhn, H. et al.: J Neurosci. 16: 2027-2033 (1996)
4. Zhu, H., Wang, Z.-Y. & Hansson, H.-A.: Brain Res. 977:180-189 (2003)
5. Gage, F. H.: Science 287: 1433-1438 (2000)
6. McNamara, R. K. et al.: Brain Res. Rev. 18: 33-49 (1993)
7. Cameron, H. A. et al.: Neuroscience 61: 203-209 (1994)
8. Cameron, H. A. et al.: Neuroscience 82: 349-354 (1998)
9. Kempermann, G. et al.: Nature 386: 493-495 (1997)
10. Lange, S et al: WO97/08202
11. Davidson, J., & Hickey, W. F.: Lab. Investigation 84: 307-319 (2004)
12. Davidson, J., & Hickey, W. F.: J. Leukocyt Biol 74: 907-919 (2004)
13. Johansson, E et al.: J Biol. Chem. 270: 20615-20620 (1995)
14. Lange, S et al.: U.S. Pat. No. 6,344,440
15. Lange, S et al: PCT/SE97/01918
16. Lange, S et al.: PCT/SE 99/02340

The invention claimed is:

1. A method of treatment of a brain injury, head trauma, an ischemic injury, asphyxia, a hypoxic injury, a traumatic injury, a stroke, and/or demyelinating disorder, associated with a pathological loss of nervous tissue, comprising administering to a patient in need thereof an effective amount of:

(a) an antisecretory factor (AF) protein as shown in SEQ ID NO: 1, and/or (b) a fragment of the AF protein as shown in SEQ ID NO: 1, said fragment consisting of an amino acid sequence as shown in SEQ ID NO:3, SEQ ID NO:4, SEQ ID NO:5, or SEQ ID NO:6, and having a histidine at position 38, a serine at position 39, and a threonine at position 41 of SEQ ID NO:3, SEQ ID NO:4, SEQ ID NO:5, or SEQ ID NO:6; and/or (c) a fragment of the AF protein as shown in SEQ ID NO: 1, said fragment consisting of amino acid nos. 1-105 of SEQ ID NO:1;

or a pharmaceutically acceptable salt thereof.

2. The method according to claim 1, wherein the condition is characterized by displaying a pathological degeneration of, loss of ability and/or loss of control of regeneration of a differentiated cell and/or tissue, an embryonic stem cell, an adult stem cell, a progenitor cell and/or a cell derived from a stem cell or progenitor cell.

3. The method according to claim 1, wherein the condition is associated with a pathological loss of cells in the peripheral, autonomic or central nervous system.

4. The method according to claim 1, wherein the condition is associated with a pathological loss of neural stem cells or neural progenitor cells.

5. The method according to claim 1, wherein the condition is associated with a pathological loss of oligodendroglial, astroglial, Schwann cells, and/or neuronal cells and/or cell populations.

6. The method according to claim 5, wherein the condition is associated with a pathological loss of non-cholinergic neuronal cells, cholinergic neuronal cells and/or glial cells, and/or cell populations.

7. The method according to claim 1, wherein the condition is caused by damage to the central nervous system or a defect in the central nervous system.

8. The method according to claim 1, wherein the condition is caused by a traumatic, auto-immune or degenerative disorder.

9. The method according to claim 1, wherein the condition is caused by axonal damage caused by concussion, contusion, axonal damage caused by head trauma, axonal damage caused by small vessel disease in the CNS and/or damage to the spinal cord after disease and/or trauma.

10. The method according to claim 1, wherein said condition is characterized by memory loss.

11. The method according to claim 1, wherein the condition is a brain injury, head trauma, and/or an ischemic injury.

12. The method according to claim 1, wherein the anti-secretory factor protein and/or fragment thereof is formulated into a medicament for intravenous infusion, intramuscular injection and/or subcutaneous injection.

\* \* \* \* \*

SEQUENCE LISTING

<160> NUMBER OF SEQ ID NOS: 6

<210> SEQ ID NO 1
<211> LENGTH: 382
<212> TYPE: PRT
<213> ORGANISM: Homo sapiens

<400> SEQUENCE: 1

-continued

```
Met Val Leu Glu Ser Thr Met Val Cys Val Asp Asn Ser Glu Tyr Met
 1               5                  10                  15

Arg Asn Gly Asp Phe Leu Pro Thr Arg Leu Gln Ala Gln Gln Asp Ala
             20                  25                  30

Val Asn Ile Val Cys His Ser Lys Thr Arg Ser Asn Pro Glu Asn Asn
         35                  40                  45

Val Gly Leu Ile Thr Leu Ala Asn Asp Cys Glu Val Leu Thr Thr Leu
     50                  55                  60

Thr Pro Asp Thr Gly Arg Ile Leu Ser Lys Leu His Thr Val Gln Pro
 65                  70                  75                  80

Lys Gly Lys Ile Thr Phe Cys Thr Gly Ile Arg Val Ala His Leu Ala
                 85                  90                  95

Leu Lys His Arg Gln Gly Lys Asn His Lys Met Arg Ile Ile Ala Phe
             100                 105                 110

Val Gly Ser Pro Val Glu Asp Asn Glu Lys Asp Leu Val Lys Leu Ala
         115                 120                 125

Lys Arg Leu Lys Lys Glu Lys Val Asn Val Asp Ile Ile Asn Phe Gly
     130                 135                 140

Glu Glu Glu Val Asn Thr Glu Lys Leu Thr Ala Phe Val Asn Thr Leu
145                 150                 155                 160

Asn Gly Lys Asp Gly Thr Gly Ser His Leu Val Thr Val Pro Pro Gly
                 165                 170                 175

Pro Ser Leu Ala Asp Ala Leu Ile Ser Ser Pro Ile Leu Ala Gly Glu
             180                 185                 190

Gly Gly Ala Met Leu Gly Leu Gly Ala Ser Asp Phe Glu Phe Gly Val
         195                 200                 205

Asp Pro Ser Ala Asp Pro Glu Leu Ala Leu Ala Leu Arg Val Ser Met
     210                 215                 220

Glu Glu Gln Arg His Ala Gly Gly Ala Arg Arg Ala Ala Arg Ala
225                 230                 235                 240

Ser Ala Ala Glu Ala Gly Ile Ala Thr Thr Gly Thr Glu Asp Ser Asp
                 245                 250                 255

Asp Ala Leu Leu Lys Met Thr Ile Ser Gln Gln Glu Phe Gly Arg Thr
             260                 265                 270

Gly Leu Pro Asp Leu Ser Ser Ser Thr Glu Glu Glu Ile Ala Tyr
         275                 280                 285

Ala Met Gln Met Ser Leu Gln Gly Ala Glu Phe Gly Gln Ala Glu Ser
     290                 295                 300

Ala Asp Ile Asp Ala Ser Ser Ala Met Asp Thr Ser Glu Pro Ala Lys
305                 310                 315                 320

Glu Glu Asp Asp Tyr Asp Val Met Gln Asp Pro Glu Phe Leu Gln Ser
                 325                 330                 335

Val Leu Glu Asn Leu Pro Gly Val Asp Pro Asn Asn Glu Ala Ile Arg
             340                 345                 350

Asn Ala Met Gly Ser Leu Pro Pro Arg Pro Arg Thr Ala Arg Arg
         355                 360                 365

Thr Arg Arg Arg Lys Thr Arg Ser Glu Thr Gly Gly Lys Gly
     370                 375                 380
```

<210> SEQ ID NO 2
<211> LENGTH: 1323
<212> TYPE: DNA
<213> ORGANISM: Homo sapiens
<220> FEATURE:
<221> NAME/KEY: CDS
<222> LOCATION: (63)..(1208)

```
<400> SEQUENCE: 2
aattggagga gttgttgtta ggccgtcccg agacccggt cgggagggag gaaggtggca      60 ag atg gtg ttg gaa agc act atg gtg tgt gtg gac aac agt gag tat      107
   Met Val Leu Glu Ser Thr Met Val Cys Val Asp Asn Ser Glu Tyr
   1               5                  10                  15 atg cgg aat gga gac ttc tta ccc acc agg ctg cag gcc cag cag gat      155
Met Arg Asn Gly Asp Phe Leu Pro Thr Arg Leu Gln Ala Gln Gln Asp
             20                  25                  30 gct gtc aac ata gtt tgt cat tca aag acc cgc agc aac cct gag aac      203
Ala Val Asn Ile Val Cys His Ser Lys Thr Arg Ser Asn Pro Glu Asn
         35                  40                  45 aac gtg ggc ctt atc aca ctg gct aat gac tgt gaa gtg ctg acc aca      251
Asn Val Gly Leu Ile Thr Leu Ala Asn Asp Cys Glu Val Leu Thr Thr
     50                  55                  60 ctc acc cca gac act ggc cgt atc ctg tcc aag cta cat act gtc caa      299
Leu Thr Pro Asp Thr Gly Arg Ile Leu Ser Lys Leu His Thr Val Gln
 65                  70                  75 ccc aag ggc aag atc acc ttc tgc acg ggc atc cgc gtg gcc cat ctg      347
Pro Lys Gly Lys Ile Thr Phe Cys Thr Gly Ile Arg Val Ala His Leu
 80                  85                  90                  95 gct ctg aag cac cga caa ggc aag aat cac aag atg cgc atc att gcc      395
Ala Leu Lys His Arg Gln Gly Lys Asn His Lys Met Arg Ile Ile Ala
                100                 105                 110 ttt gtg gga agc cca gtg gag gac aat gag aag gat ctg gtg aaa ctg      443
Phe Val Gly Ser Pro Val Glu Asp Asn Glu Lys Asp Leu Val Lys Leu
            115                 120                 125 gct aaa cgc ctc aag aag gag aaa gta aat gtt gac att atc aat ttt      491
Ala Lys Arg Leu Lys Lys Glu Lys Val Asn Val Asp Ile Ile Asn Phe
        130                 135                 140 ggg gaa gag gag gtg aac aca gaa aag ctg aca gcc ttt gta aac acg      539
Gly Glu Glu Glu Val Asn Thr Glu Lys Leu Thr Ala Phe Val Asn Thr
    145                 150                 155 ttg aat ggc aaa gat gga acc ggt tct cat ctg gtg aca gtg cct cct      587
Leu Asn Gly Lys Asp Gly Thr Gly Ser His Leu Val Thr Val Pro Pro
160                 165                 170                 175 ggg ccc agt ttg gct gat gct ctc atc agt tct ccg att ttg gct ggt      635
Gly Pro Ser Leu Ala Asp Ala Leu Ile Ser Ser Pro Ile Leu Ala Gly
                180                 185                 190 gaa ggt ggt gcc atg ctg ggt ctt ggt gcc agt gac ttt gaa ttt gga      683
Glu Gly Gly Ala Met Leu Gly Leu Gly Ala Ser Asp Phe Glu Phe Gly
            195                 200                 205 gta gat ccc agt gct gat cct gag ctg gcc ttg gcc ctt cgt gta tct      731
Val Asp Pro Ser Ala Asp Pro Glu Leu Ala Leu Ala Leu Arg Val Ser
        210                 215                 220 atg gaa gag cag cgg cac gca gga gga gga gcg cgg cgg gca gct cga      779
Met Glu Glu Gln Arg His Ala Gly Gly Gly Ala Arg Arg Ala Ala Arg
    225                 230                 235 gct tct gct gct gag gcc ggg att gct acg act ggg act gaa gac tca      827
Ala Ser Ala Ala Glu Ala Gly Ile Ala Thr Thr Gly Thr Glu Asp Ser
240                 245                 250                 255 gac gat gcc ctg ctg aag atg acc atc agc cag caa gag ttt ggc cgc      875
Asp Asp Ala Leu Leu Lys Met Thr Ile Ser Gln Gln Glu Phe Gly Arg
                260                 265                 270 act ggg ctt cct gac cta agc agt agt act gag gaa gag gag att gct      923
Thr Gly Leu Pro Asp Leu Ser Ser Ser Thr Glu Glu Glu Glu Ile Ala
            275                 280                 285 tat gcc atg cag atg tcc ctg cag gga gca gag ttt ggc cag gcg gaa      971
Tyr Ala Met Gln Met Ser Leu Gln Gly Ala Glu Phe Gly Gln Ala Glu
        290                 295                 300
```

```
tca gca gac att gat gcc agc tca gct atg gac aca tct gag cca gcc    1019
Ser Ala Asp Ile Asp Ala Ser Ser Ala Met Asp Thr Ser Glu Pro Ala
    305                 310                 315 aag gag gag gat gat tac gac gtg atg cag gac ccc gag ttc ctt cag    1067
Lys Glu Glu Asp Asp Tyr Asp Val Met Gln Asp Pro Glu Phe Leu Gln
320                 325                 330                 335 agt gtc cta gag aac ctc cca ggt gtg gat ccc aac aat gaa gcc att    1115
Ser Val Leu Glu Asn Leu Pro Gly Val Asp Pro Asn Asn Glu Ala Ile
                340                 345                 350 cga aat gct atg ggc tcc ctg cct ccc agg cca cca agg acg gca aga    1163
Arg Asn Ala Met Gly Ser Leu Pro Pro Arg Pro Pro Arg Thr Ala Arg
            355                 360                 365 agg aca aga agg agg aag aca aga agt gag act gga ggg aaa ggg        1208
Arg Thr Arg Arg Arg Lys Thr Arg Ser Glu Thr Gly Gly Lys Gly
        370                 375                 380 tagctgagtc tgcttagggg actgggaagc acgaaatata gggttagatg tggttatctg  1268
taaccattac agcctaaata aagcttggca acttttaaaa aaaaaaaaaa aaaaa       1323

<210> SEQ ID NO 3
<211> LENGTH: 46
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (1)..(35)
<223> OTHER INFORMATION: This region may or may not be present
<220> FEATURE:
<221> NAME/KEY: MOD_RES
<222> LOCATION: (38)
<223> OTHER INFORMATION: His, Arg or Lys
<220> FEATURE:
<221> NAME/KEY: MOD_RES
<222> LOCATION: (39)
<223> OTHER INFORMATION: Ser or Leu
<220> FEATURE:
<221> NAME/KEY: MOD_RES
<222> LOCATION: (41)
<223> OTHER INFORMATION: Thr or Ala
<220> FEATURE:
<221> NAME/KEY: MOD_RES
<222> LOCATION: (43)..(46)
<223> OTHER INFORMATION: This region may or may not be present

<400> SEQUENCE: 3

Met Val Leu Glu Ser Thr Met Val Cys Val Asp Asn Ser Glu Tyr Met
1               5                   10                  15

Arg Asn Gly Asp Phe Leu Pro Thr Arg Leu Gln Ala Gln Gln Asp Ala
                20                  25                  30

Val Asn Ile Val Cys Xaa Xaa Lys Xaa Arg Ser Asn Pro Glu
            35                  40                  45

<210> SEQ ID NO 4
<211> LENGTH: 51
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (1)..(35)
<223> OTHER INFORMATION: This region may or may not be present
<220> FEATURE:
<221> NAME/KEY: MOD_RES
<222> LOCATION: (38)
```

```
<223> OTHER INFORMATION: His, Arg or Lys
<220> FEATURE:
<221> NAME/KEY: MOD_RES
<222> LOCATION: (39)
<223> OTHER INFORMATION: Ser or Leu
<220> FEATURE:
<221> NAME/KEY: MOD_RES
<222> LOCATION: (41)
<223> OTHER INFORMATION: Thr or Ala
<220> FEATURE:
<221> NAME/KEY: MOD_RES
<222> LOCATION: (43)..(51)
<223> OTHER INFORMATION: This region may or may not be present

<400> SEQUENCE: 4

Met Val Leu Glu Ser Thr Met Val Cys Val Asp Asn Ser Glu Tyr Met
 1               5                  10                  15

Arg Asn Gly Asp Phe Leu Pro Thr Arg Leu Gln Ala Gln Gln Asp Ala
            20                  25                  30

Val Asn Ile Val Cys Xaa Xaa Lys Xaa Arg Ser Asn Pro Glu Asn Asn
        35                  40                  45

Val Gly Leu
    50

<210> SEQ ID NO 5
<211> LENGTH: 80
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (1)..(35)
<223> OTHER INFORMATION: This region may or may not be present
<220> FEATURE:
<221> NAME/KEY: MOD_RES
<222> LOCATION: (38)
<223> OTHER INFORMATION: His, Arg or Lys
<220> FEATURE:
<221> NAME/KEY: MOD_RES
<222> LOCATION: (39)
<223> OTHER INFORMATION: Ser or Leu
<220> FEATURE:
<221> NAME/KEY: MOD_RES
<222> LOCATION: (41)
<223> OTHER INFORMATION: Thr or Ala
<220> FEATURE:
<221> NAME/KEY: MOD_RES
<222> LOCATION: (43)..(80)
<223> OTHER INFORMATION: This region may or may not be present

<400> SEQUENCE: 5

Met Val Leu Glu Ser Thr Met Val Cys Val Asp Asn Ser Glu Tyr Met
 1               5                  10                  15

Arg Asn Gly Asp Phe Leu Pro Thr Arg Leu Gln Ala Gln Gln Asp Ala
            20                  25                  30

Val Asn Ile Val Cys Xaa Xaa Lys Xaa Arg Ser Asn Pro Glu Asn Asn
        35                  40                  45

Val Gly Leu Ile Thr Leu Ala Asn Asp Cys Glu Val Leu Thr Thr Leu
    50                  55                  60

Thr Pro Asp Thr Gly Arg Ile Leu Ser Lys Leu His Thr Val Gln Pro
65                  70                  75                  80

<210> SEQ ID NO 6
<211> LENGTH: 163
<212> TYPE: PRT
<213> ORGANISM: Artificial Sequence
<220> FEATURE:
```

```
<223> OTHER INFORMATION: Description of Artificial Sequence: Synthetic
      amino acid sequence
<220> FEATURE:
<221> NAME/KEY: MOD_RES
<222> LOCATION: (1)..(35)
<223> OTHER INFORMATION: This region may or may not be present
<220> FEATURE:
<221> NAME/KEY: MOD_RES
<222> LOCATION: (38)
<223> OTHER INFORMATION: His, Arg or Lys
<220> FEATURE:
<221> NAME/KEY: MOD_RES
<222> LOCATION: (39)
<223> OTHER INFORMATION: Ser or Leu
<220> FEATURE:
<221> NAME/KEY: MOD_RES
<222> LOCATION: (41)
<223> OTHER INFORMATION: Thr or Ala
<220> FEATURE:
<221> NAME/KEY: MOD_RES
<222> LOCATION: (43)..(163)
<223> OTHER INFORMATION: This region may or may not be present

<400> SEQUENCE: 6

Met Val Leu Glu Ser Thr Met Val Cys Val Asp Asn Ser Glu Tyr Met
 1               5                  10                  15

Arg Asn Gly Asp Phe Leu Pro Thr Arg Leu Gln Ala Gln Gln Asp Ala
                20                  25                  30

Val Asn Ile Val Cys Xaa Xaa Lys Xaa Arg Ser Asn Pro Glu Asn Asn
                35                  40                  45

Val Gly Leu Ile Thr Leu Ala Asn Asp Cys Glu Val Leu Thr Thr Leu
    50                  55                  60

Thr Pro Asp Thr Gly Arg Ile Leu Ser Lys Leu His Thr Val Gln Pro
65                  70                  75                  80

Lys Gly Lys Ile Thr Phe Cys Thr Gly Ile Arg Val Ala His Leu Ala
                85                  90                  95

Leu Lys His Arg Gln Gly Lys Asn His Lys Met Arg Ile Ile Ala Phe
                100                 105                 110

Val Gly Ser Pro Val Glu Asp Asn Glu Lys Asp Leu Val Lys Leu Ala
                115                 120                 125

Lys Arg Leu Lys Lys Glu Lys Val Asn Val Asp Ile Ile Asn Phe Gly
                130                 135                 140

Glu Glu Glu Val Asn Thr Glu Lys Leu Thr Ala Phe Val Asn Thr Leu
145                 150                 155                 160

Asn Gly Lys
```